(12) United States Patent
Fortin

(10) Patent No.: US 7,214,061 B2
(45) Date of Patent: May 8, 2007

(54) UNIVERSAL TEETH PROSTHESIS AND METHOD OF MANUFACTURING THEREOF

(75) Inventor: Yvan Fortin, Sainte-Foy (CA)

(73) Assignee: Marius Limited (BB)

( * ) Notice: Subject to any disclaimer, the term of this patent is extended or adjusted under 35 U.S.C. 154(b) by 0 days.

(21) Appl. No.: 10/648,700

(22) Filed: Aug. 26, 2003

(65) Prior Publication Data

US 2004/0038181 A1  Feb. 26, 2004

(30) Foreign Application Priority Data

Aug. 26, 2002 (CA) .................................. 2399740

(51) Int. Cl.
*A61C 8/00* (2006.01)

(52) U.S. Cl. ..................................................... 433/173

(58) Field of Classification Search ................ 433/173, 433/172, 174, 168.1, 170, 194, 193, 200.1, 433/181

See application file for complete search history.

(56) References Cited

U.S. PATENT DOCUMENTS

| 4,085,506 A | 4/1978 | Lew .................................. 32/2 |
| 4,225,668 A * | 9/1980 | Bartoli ........................ 433/176 |
| 4,767,328 A * | 8/1988 | Branemark ............... 433/168.1 |
| 5,221,206 A * | 6/1993 | Nardi .......................... 433/193 |
| 5,429,505 A | 7/1995 | Fortin ......................... 433/172 |
| 5,575,651 A | 11/1996 | Weissman ................... 433/173 |
| 5,674,070 A | 10/1997 | Fortin et al. ................ 433/172 |
| 6,322,364 B1 | 11/2001 | Oshida et al. .............. 433/173 |

FOREIGN PATENT DOCUMENTS

DE  9731658  12/1998

* cited by examiner

*Primary Examiner*—Melba Bumgarner
(74) *Attorney, Agent, or Firm*—Merchant & Gould P.C.

(57) ABSTRACT

A teeth prosthesis for mounting thereon a member having a set of teeth has at least three implants, each implant having opposite ends, one end of each implant being anchored in a bone of a maxilla while an opposite end projects out of a gingiva and defines a head. A customized connecting bar is also provided, the connecting bar being shaped and sized to substantially conform to and face the gingiva and fastened to the implants. A pair of mating bars having standardized sizes and shapes are also provided, consisting of a meso-bar fastened to the connecting bar and an iso-bar removably attached to the meso-bar through an attachment. The teeth prosthesis of the present invention is more economical to produce than prior art devices since it makes use of customized components and only the connecting bar is adjusted for a specific person.

7 Claims, 6 Drawing Sheets

UNIVERSAL TEETH PROSTHESIS AND METHOD OF MANUFACTURING THEREOF

FIELD OF THE INVENTION

The present invention relates to an improved teeth prosthesis for an upper maxilla or a lower maxilla, and more particularly to a new design of a triple structure teeth prosthesis permitting an improved precision over existing prostheses. Moreover, as will become apparent hereinafter, the design of the present invention will allow most dental laboratories to use the technology described herein.

BACKGROUND OF THE INVENTION

It is well known in the art to provide a teeth prosthesis for a lower or an upper maxilla, the teeth prosthesis being of the type comprising an infrastructure, a suprastructure and means for removable attachment of the suprastructure with the infrastructure.

More particularly, U.S. Pat. No. 5,429,505 (FORTIN) and U.S. Pat. No. 5,674,070 (FORTIN), which is a continuation-in-part of U.S. Pat. No. 5,429,505, relate to a teeth prosthesis, a method of manufacture thereof and a method for mounting and removing a suprastructure thereof. These patents disclose a teeth prosthesis for an upper maxilla including an infrastructure, a suprastructure, and an assembly for removable attachment of the suprastructure with the infrastructure. The infrastructure includes at least three implants, one connection bar, and an assembly for removably fastening the connection bar with and against the head of each of the implants. The suprastructure includes a first member made of cast metal or alloy having an intrados provided with an opening giving access to a housing of such size and depth to allow the housing of the connection bar therein, a second member permanently attached to the first member, and a set of teeth fixed to the first member and the second member. The assembly includes two first fastening members, and a second fastening member. The invention is also directed to a method for the manufacture of such a teeth prosthesis.

However, even though aforesaid prior art teeth prosthesis can perform correctly when installed on the lower or the upper maxilla, the different elements of the teeth prosthesis have to be specifically machined to fit in each user's mouth. This machining involves a very high production cost because each element of the prosthesis must be customised for each user. Moreover, the involved machining procedure is very complicated and it has been demonstrated that the manufacture of such a teeth prosthesis is extremely difficult from a technical point of view. Furthermore, if a user loses an implant, it is actually quite difficult and expensive to replace it, or even impossible with appropriate precision, since all elements are customised. In most cases, the whole assembly must be replaced.

Therefore, there is a need to provide a teeth prosthesis wherein most of the elements are not customised, but are standard. This would allow supplying a more accurate teeth prosthesis to the user at an equivalent or cheaper cost. Moreover, this would also allow providing such a new technology available for most dental laboratories. Furthermore, since the elements of the prosthesis are not customised parts, it would be faster and cheaper to repair the teeth prosthesis with the same precision as the existing prosthesis.

SUMMARY OF THE INVENTION

An object of the present invention is to provide a teeth prosthesis which is more flexible and accessible.

Another object of the present invention is to provide a teeth prosthesis wherein some elements can be replaced with substantially the same precision in case a break occurs.

More specifically, the invention relates to a teeth prosthesis for mounting thereon a member having a set of teeth, said teeth prosthesis comprising:

- at least three implants, each implant having opposite ends, one end of each implant being anchored in a bone of a maxilla while an opposite end projects out of a gingiva and defines a head;
- a customized connecting bar being shaped and sized to substantially conform to and face the gingiva and fastened to said implants;
- a pair of mating bars having a predetermined size and shape selected from a plurality of predetermined sizes and shapes, said pair of mating bars comprising a meso-bar fastened to said connecting bar and an iso-bar removably attached to said meso-bar with attaching means, said iso-bar being adapted to receive said member.

The present invention and its advantages will be better understood upon reading of preferred embodiments thereof with reference to appended drawings.

BRIEF DESCRIPTION OF THE DRAWINGS

A detailed description of preferred embodiments will be given herein below with reference to the following drawings, in which like numbers refer to like elements.

DETAILED DESCRIPTION OF A PREFERRED EMBODIMENT OF THE INVENTION

Figure 1:
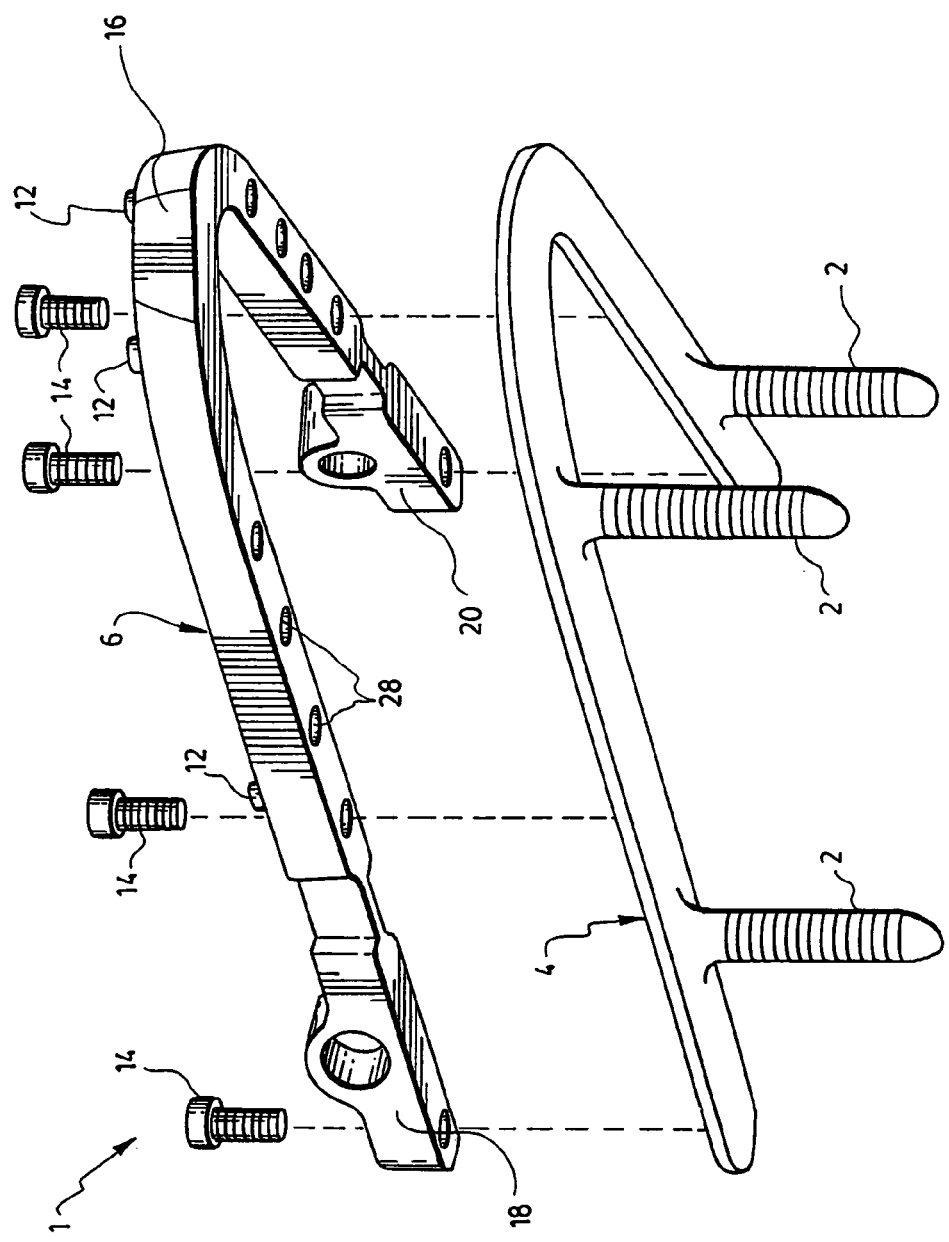
FIG. 1 is a perspective view of a connecting bar onto which a meso-bar is mounted according to a preferred embodiment of the present invention.
Figure 2:
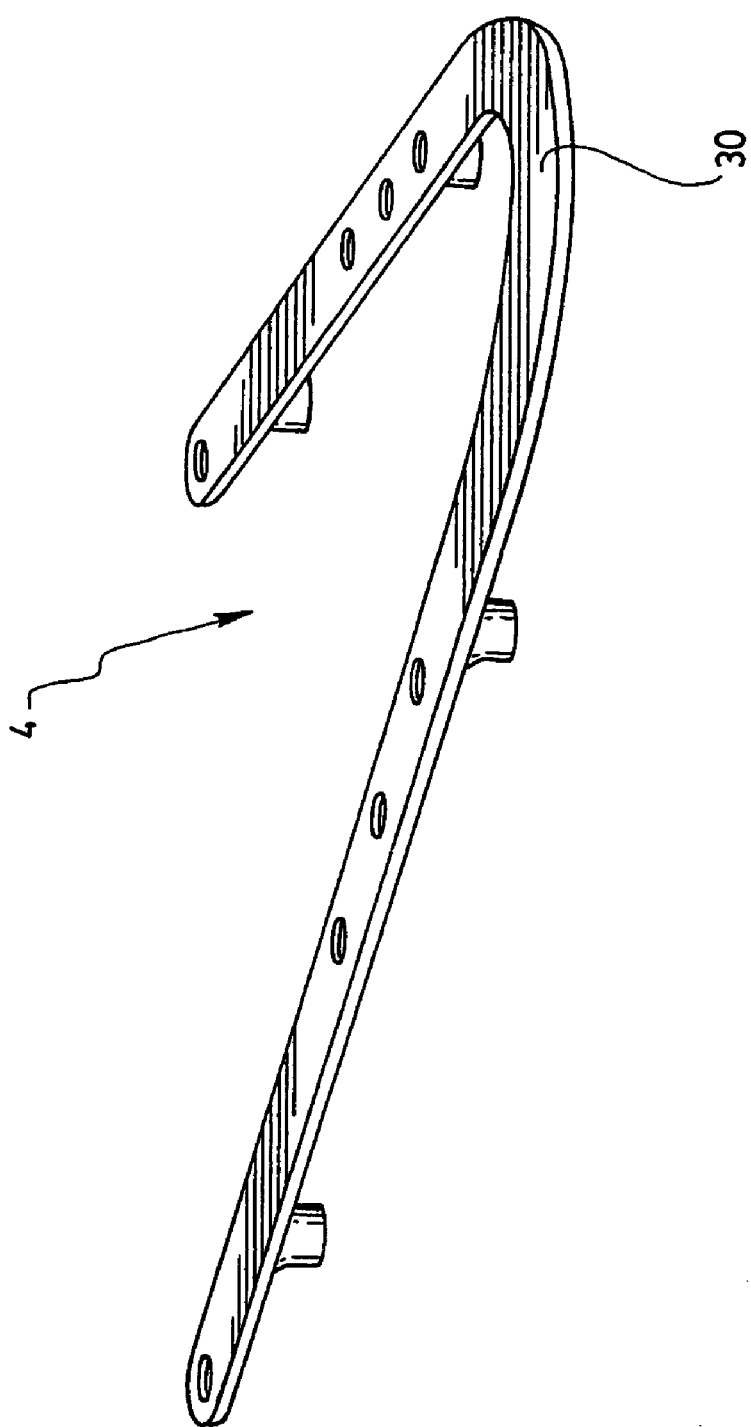
FIG. 2 is a perspective view of the connecting bar of FIG. 1.
Figure 3:
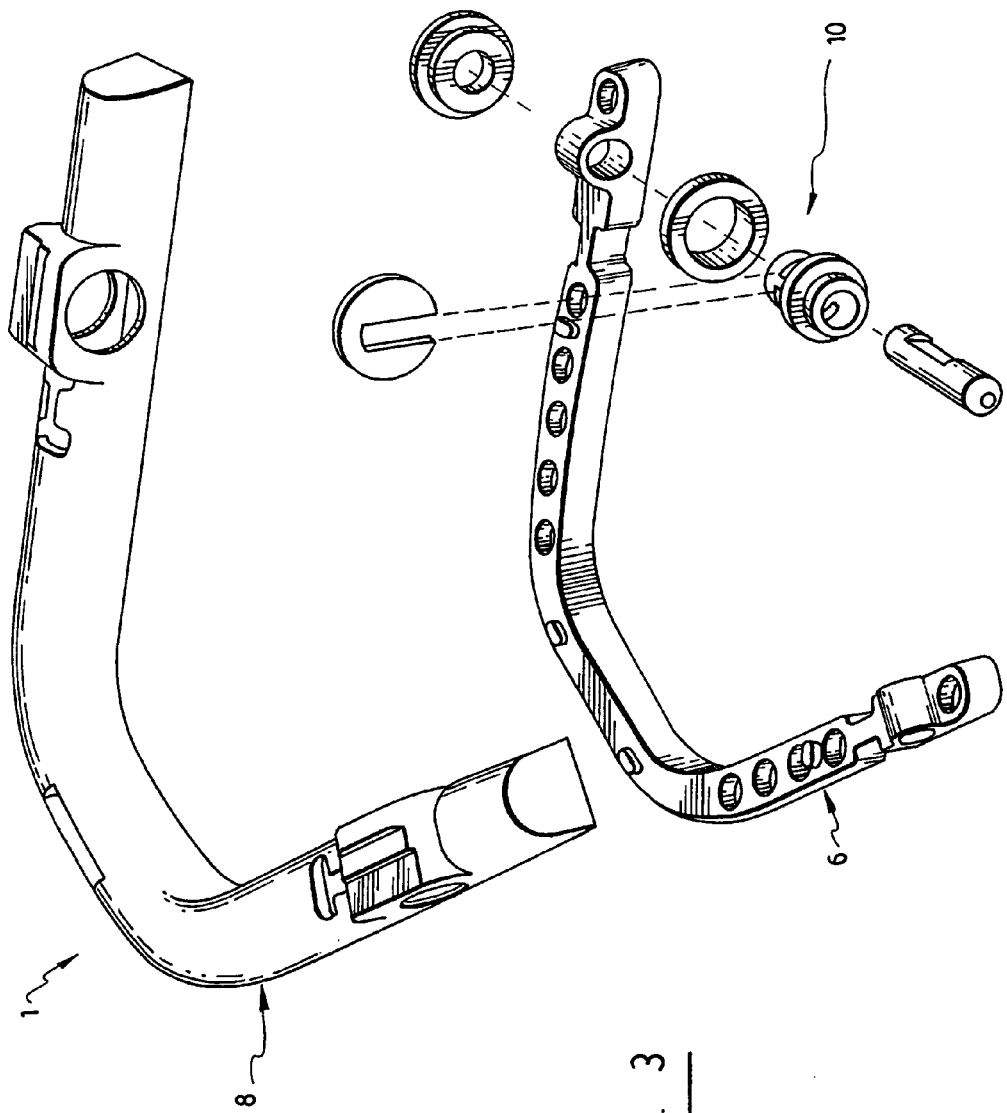
FIG. 3 is an exploded perspective view of a meso-bar and an iso-bar of according to a preferred embodiment of the present invention.

Referring to FIGS. 1, 2 and 3, there is shown the different elements of a teeth prosthesis 1 according to the present invention. The teeth prosthesis 1 comprises at least three implants 2 (as shown in FIG. 1) and preferably four to six, each implant 2 having opposite ends, one end of each implant being anchored in a bone of a maxilla while an opposite end protrudes out of a gingiva and defines a head.

The teeth prosthesis 1 also comprises a customized connecting bar 4 shaped and sized to be substantially facing the gingiva and to conform to the shape of the gingiva. The connecting bar 4 is fastened to the implants 2 through conventional and usual means. As can be appreciated on FIGS. 1 and 2, the connecting bar 4 is a very thin structure which is attachable to the maxilla through the implants. The connecting bar 4 is preferably provided with an extremely flat top part 30 and is preferably shaped and sized to receive components of predetermined sizes, as will be explained hereafter.

It should be noted that the connecting bar 4 is fastened to the implants only after it has been adjusted to the mouth of the user and to ensure that it is passive, i.e. that it does not create any pressure or tension on the implants and thus, on the maxilla which would otherwise cause pain and discomfort to the patient.

The teeth prosthesis 1 also comprises a pair of mating bars. The mating bars have a predetermined shape and size selected from a plurality of predetermined shapes and sizes, the purpose of which will be explained hereinafter. The pair of mating bars includes a meso-bar 6 shaped and sized to substantially face the connecting bar 4 and adapted to be fastened thereto and a iso-bar 8. The mating bars are removably attached together through attaching devices 10 (as shown in FIG. 3). Alternatively, one could conceive mating bars that do not require attaching devices per se, but are so shaped and sized, that they are held together by friction, for example. Consequently, the term "attaching means" includes a friction fit, and other similar ways to attach the bars together. An element having a set of teeth mounted thereon (not shown) can be mounted onto the triple structure teeth prosthesis 1 as known in the art, and more particularly in U.S. Pat. No. 5,674,070.

Figure 4:
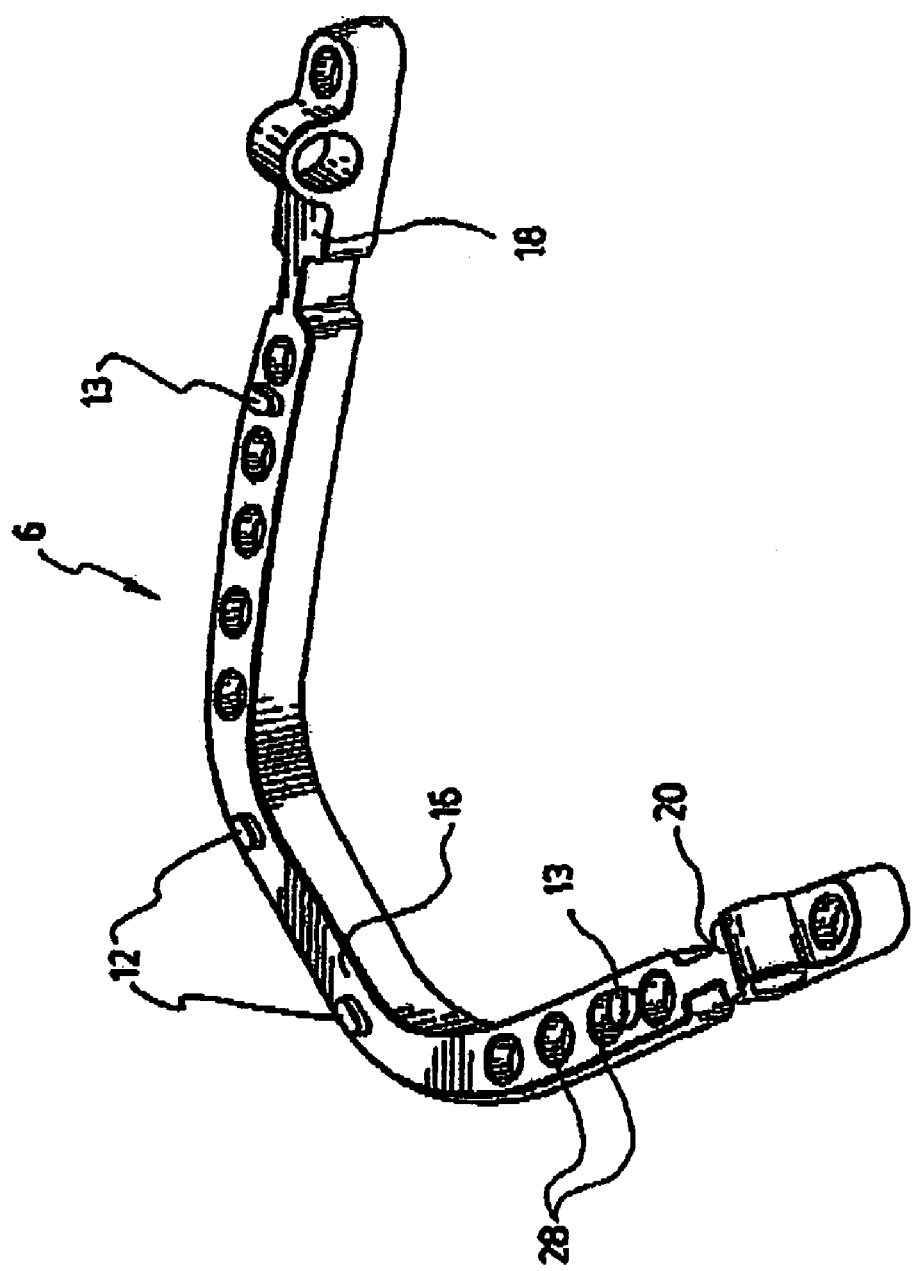
FIG. 4 is a perspective view of a meso-bar according to a preferred embodiment of the present invention.
Figure 5:
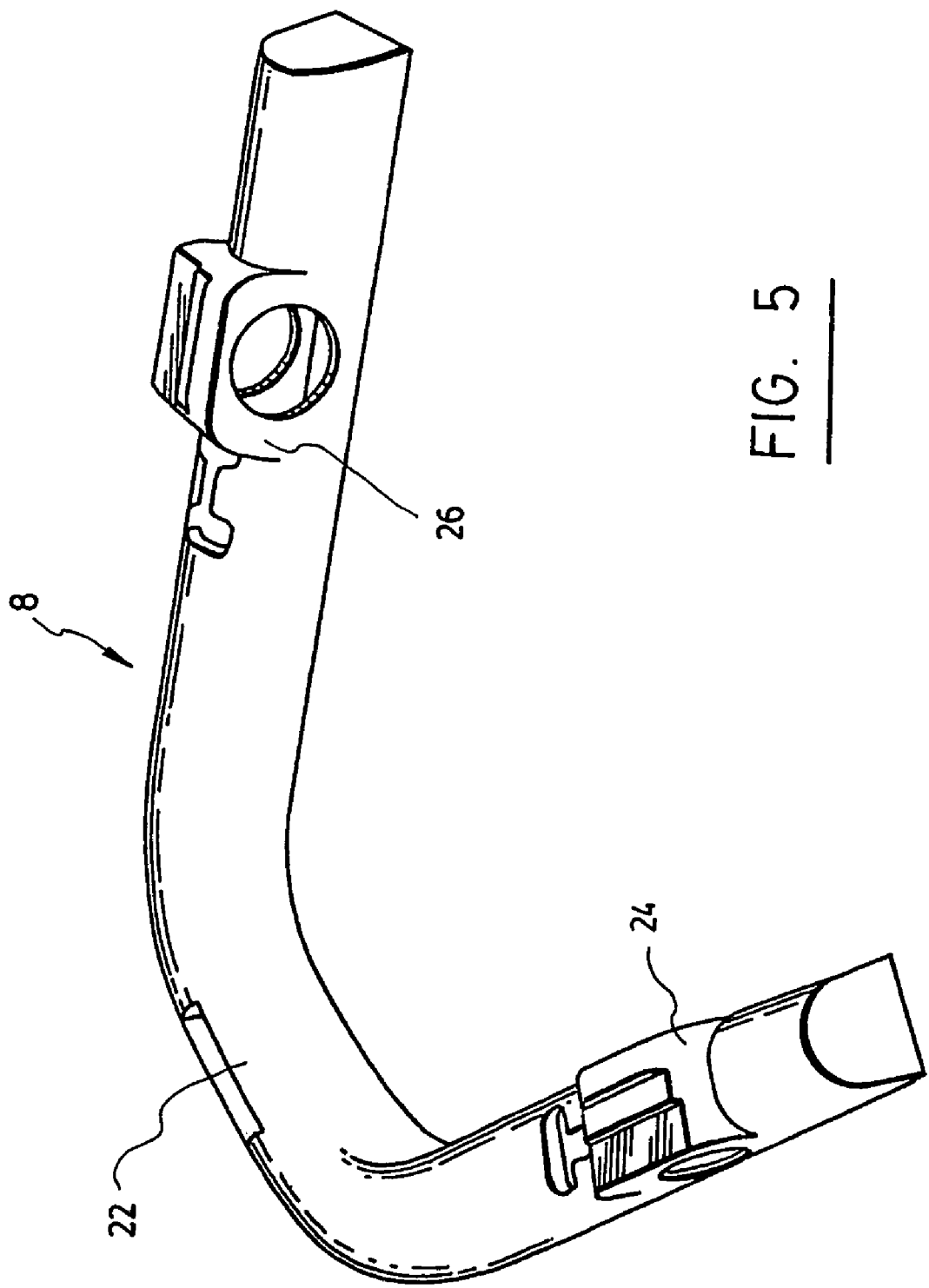
FIG. 5 is a top perspective view of the iso-bar according to a preferred embodiment of the invention.

"Referring now to FIG. 4, the meso-bar 6 has substantially the same shape as the connecting bar 4 (as better seen in FIG. 1) and comprises a fore part 16 and two opposite rear ends 18, 20. The meso-bar 6 is provided with a set of support points 12 for supporting the iso-bar 8. The iso-bar 8 is also provided with a set of support points 13 (as shown in FIG. 4). The support points 12, 13 define an anterior and a posterior support point on each side of the meso-bar 6 and the iso-bar 8. The meso-bar 6 is also provided with a plurality of fixation holes 28 and is rigidly attached onto the connecting bar 4 with at least four fasteners 14, possibly five or six, inserted and secured in the fixation holes 28. For example, screws may be used to do so. If needed, other convenient fixation holes may be drilled in the meso-bar 6.

Figure 6:
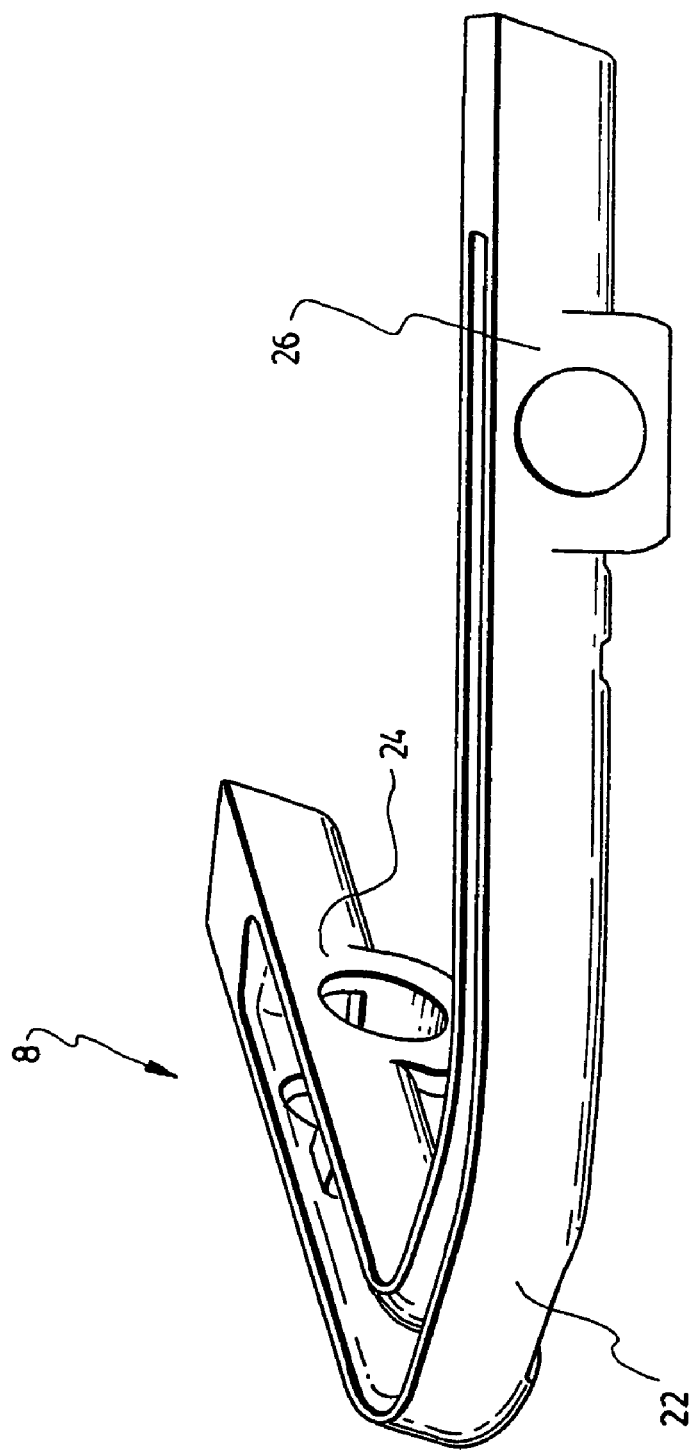
FIG. 6 is a bottom perspective view of the iso-bar of FIG. 5.

Referring now to FIG. 6, the iso-bar 8 preferably has a shape that is complementary to that of the meso-bar 6, and in fact preferably has a hollow shape, and is provided with a fore part 22 and two opposite rear ends 24, 26. As mentioned previously, the iso-bar 8 is preferably hollow and has a predetermined size and depth to receive the meso-bar 6 therein (as shown in FIG. 6).

It is preferred to use the attaching devices 10 for fastening the iso-bar 8 onto the meso-bar 6 shown in FIG. 3. However, any other means for removably attaching the meso-bar and the iso-bar together will meet the objects of the present invention and will have no impact on the way the invention works, other than perhaps loss (or increase) of precision. As an example, clips or other types of attaching devices will meet the objects of the invention.

The attaching devices 10 according to a preferred embodiment of the invention are machined for providing a high degree of precision, and a precision of at least 5 microns has been achieved. In the past, such attaching devices were die cast and reached a precision of approximately 50 microns. Preferably, the attaching devices 10 comprise two posterior closure piston systems, well known in the art, but other convenient fasteners may be used. These two attaching devices 10 are respectively attached with a corresponding rear end 24, 26 of the iso-bar 8 for removably attaching them with corresponding ends 18, 20 of the meso-bar 6.

The set of support points 12 of the meso-bar 6 and the set of support points 13 of the iso-bar 8 allow the correct adjustment of both bars together.

Preferably, the connecting bar 4 is made of gold or palladium; and the meso-bar 6 and the iso-bar 8 are made of titanium. The attaching devices 10 are also preferably made of palladium, titanium or other appropriate materials.

As mentioned previously, the meso-bar 6 and the iso-bar 8 are standardized in that they are provided in several predetermined sizes, preferably three, and are not custom made. The connecting bar 4 is the only customized part for correctly adjusting it on the gingiva of the user.

In practice, the implants are fixed to the maxilla and the connecting bar 4 is attached to the implants. A technician then uses a gauge based on the predetermined size and shape of the selected meso-bar 6 to drill the screwing holes in the connecting bar 4 at locations corresponding to the fixation holes 28 of the meso-bar 6. The flatness of the top part 30 of the connecting bar 4 permits a very accurate adjustment of the gauge thereon.

Then, the meso-bar is fastened to the connecting bar and the iso-bar removably fastened thereto.

Consequently, the use of three structures, instead of two as was the case in the past, avoids custom machining of each part of the teeth prosthesis, and allows to greatly increase the accuracy of the positioning of each element regarding the others. More specifically, teeth prostheses of the prior art reach an accuracy of 25 to 50 microns for the positioning of the different elements, while the present invention reaches at least 5 microns accuracy positioning.

Finally, the use of a three structure prosthesis, standard components and high accuracy renders the technology within the reach of dental laboratories, which was not the case in the prior art, given the exacting nature of custom made components.

In summary, the present invention teaches a first component which is custom-made and fixed to implants, and a pair of components which are manufactured in predetermined sizes to be attached to the custom component.

While embodiments of this invention have been illustrated in the accompanying drawings and described above, it will be evident to those skilled in the art that changes and modifications may be made therein without departing from the essence of this invention. All such modifications or variations are believed to be within the scope of the invention. Specifically, although bars that fit within another are illustrated, any pair of mating bar not designed to fit one within the other will meet the objects of the invention.

What is claimed is:

1. A teeth prosthesis for mounting thereon a member having a set of teeth, said teeth prosthesis comprising:
    at least three implants, each implant having apposite ends, one end of each implant being configured to be anchored in a bone of a maxilla while an opposite end is configured to project out of a gingiva and defines a head;
    a customized connecting bar being shaped and sized to substantially conform to and face the gingiva and fastened to said implants;
    a pair of standard mating bars having a predetermined size and shape and each having a fore part and two opposite rear ends, defining a shape similar to a shape of said maxilla, said pair of mating bars comprising a meso-bar fastened to said connecting bar and an iso-bar removably attached to said meso-bar with attaching means, said iso-bar being hollow and defining an opening shaped and sized to receive said meso-bar therein.

2. A teeth prosthesis according to claim 1, wherein said pair of standard mating bars have a predetermined size and shape selected from a plurality of predetermined sizes and shapes and wherein said plurality of predetermined sizes and shapes includes three predetermined sizes and shapes.

3. A teeth prosthesis according to claim 1, wherein said connecting bar has a flat top part.

4. A teeth prosthesis according to claim 3, wherein said meso-bar has a flat bottom part.

5. A teeth prosthesis according to claim 1, wherein said meso-bar is fastened to said connecting bar with at least four fasteners.

6. A teeth prosthesis according to claim 1, wherein said connecting bar is made from gold or palladium.

7. A teeth prosthesis according to claim 1, wherein said meso-bar and said iso-bar are made from titanium.

* * * * *